United States Patent [19]
Howell

[11] Patent Number: 5,911,705
[45] Date of Patent: Jun. 15, 1999

[54] ONE STEP CATHETER ADVANCEMENT AUTOMATIC NEEDLE RETRACTION SYSTEM

[75] Inventor: Glade H. Howell, Sandy, Utah

[73] Assignee: Becton Dickinson and Company, Franklin Lakes, N.J.

[21] Appl. No.: 09/074,840

[22] Filed: May 8, 1998

Related U.S. Application Data

[63] Continuation of application No. 08/628,040, Apr. 4, 1996.

[51] Int. Cl.[6] .................................................. A61M 5/00
[52] U.S. Cl. .......................... 604/110; 604/164; 604/198; 604/263
[58] Field of Search ..................................... 604/164, 158, 604/165, 195, 198, 110, 263, 192

[56] References Cited

U.S. PATENT DOCUMENTS

| | | | |
|---|---|---|---|
| 4,747,831 | 5/1988 | Kulli | 604/110 |
| 4,762,516 | 8/1988 | Luther et al. | 604/164 |
| 4,767,413 | 8/1988 | Haber et al. | 604/198 |
| 4,834,718 | 5/1989 | McDonald | 604/195 |
| 4,904,242 | 2/1990 | Kulli | 604/110 |
| 4,927,414 | 5/1990 | Kulli | 604/110 |
| 4,944,728 | 7/1990 | Carrell et al. | 604/164 |
| 4,950,252 | 8/1990 | Luther et al. | 604/198 |
| 4,973,316 | 11/1990 | Dysarz | 604/164 |
| 4,978,344 | 12/1990 | Dombrowski et al. | 604/198 |
| 4,994,041 | 2/1991 | Dombrowski et al. | 604/164 |
| 4,994,042 | 2/1991 | Vadher | 604/165 |
| 5,104,384 | 4/1992 | Parry | 604/192 |
| 5,125,414 | 6/1992 | Dysarz | 128/763 |
| 5,129,884 | 7/1992 | Dysarz | 604/164 |
| 5,195,983 | 3/1993 | Boese | 604/110 X |
| 5,312,361 | 5/1994 | Zadini et al. | 604/165 |
| 5,336,199 | 8/1994 | Castillo et al. | 604/198 |
| 5,376,075 | 12/1994 | Haughton et al. | 604/158 |
| 5,407,431 | 4/1995 | Botich et al. | 604/110 |
| 5,411,486 | 5/1995 | Zadini et al. | 604/198 |
| 5,419,766 | 5/1995 | Chang et al. | 604/110 |
| 5,425,718 | 6/1995 | Tay et al. | 604/165 |
| 5,501,675 | 3/1996 | Erskine | 604/165 X |

FOREIGN PATENT DOCUMENTS

| | | |
|---|---|---|
| 0 290 176 A1 | 11/1988 | European Pat. Off. . |
| 0 639 386 A1 | 2/1995 | European Pat. Off. . |
| 0 653 220 A1 | 5/1995 | European Pat. Off. . |
| 0 730 880 A1 | 9/1996 | European Pat. Off. . |

*Primary Examiner*—John D. Yasko
*Attorney, Agent, or Firm*—Eric M. Lee

[57] ABSTRACT

The one step catheter advancement automatic needle retraction system of this invention includes a generally hollow barrel, a needle hub which can include a flashback chamber disposed in the barrel, a secondary flashback chamber disposed in the barrel, a biasing mechanism for retracting the needle into the barrel and a clip associated with the secondary flashback chamber for engaging a catheter hub. The needle hub in conjunction with the secondary flashback chamber retain the needle in the extended position against the force of the biasing mechanism until the catheter has been advanced a certain distance from the distal end of the barrel.

12 Claims, 6 Drawing Sheets

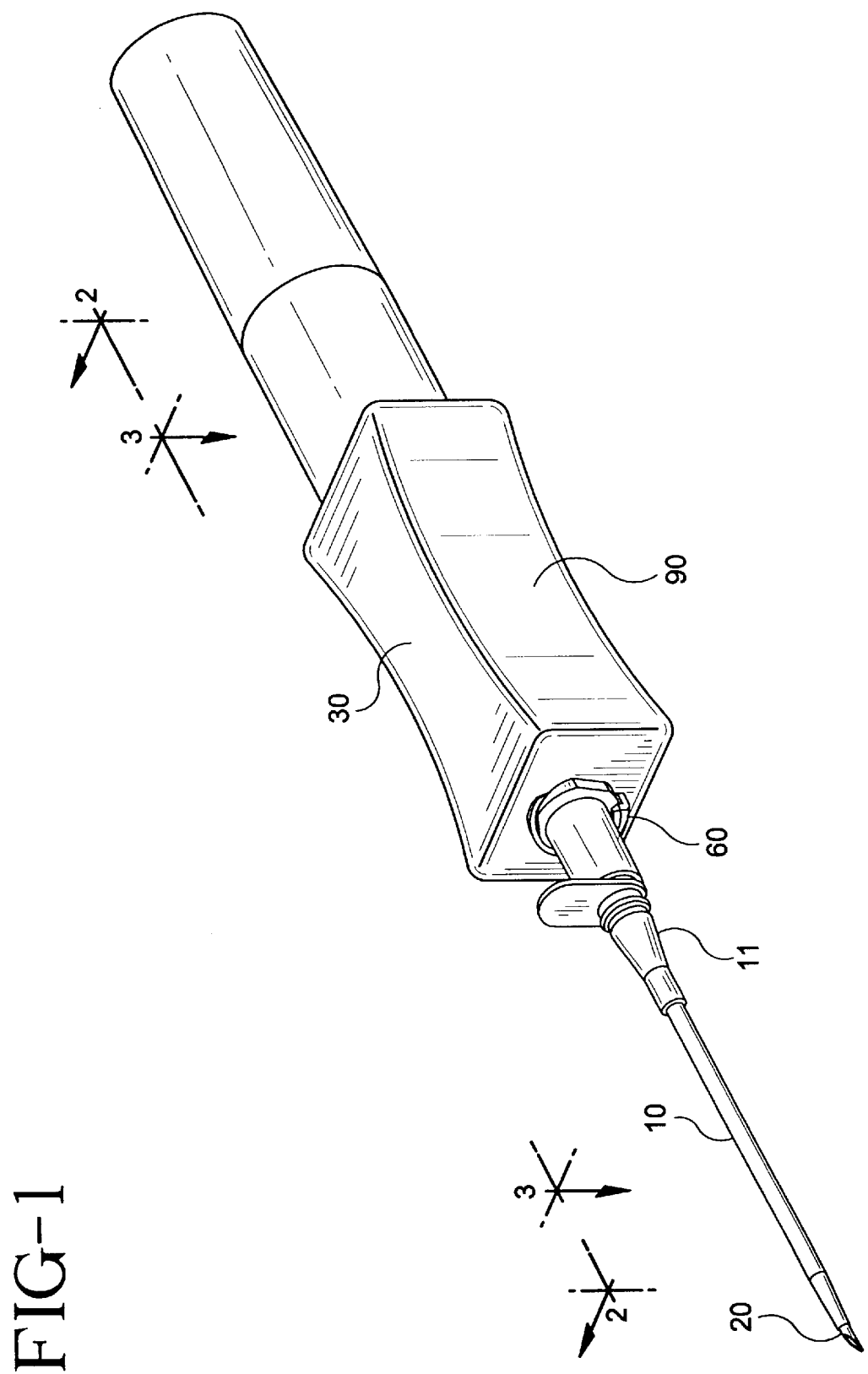

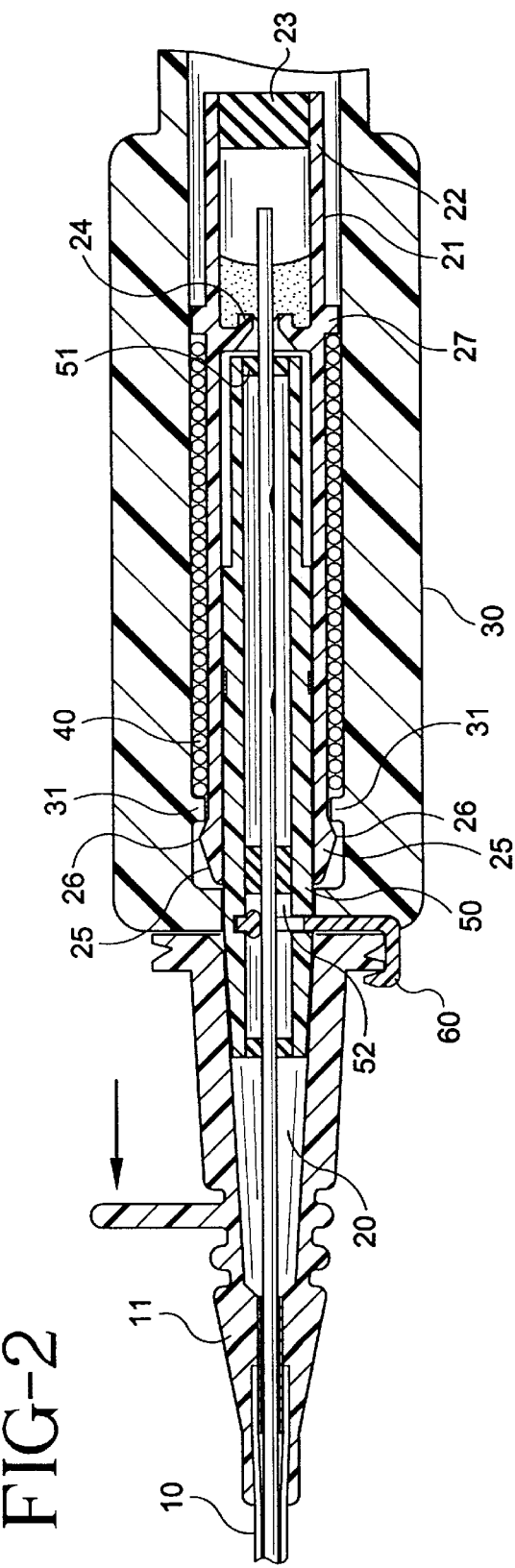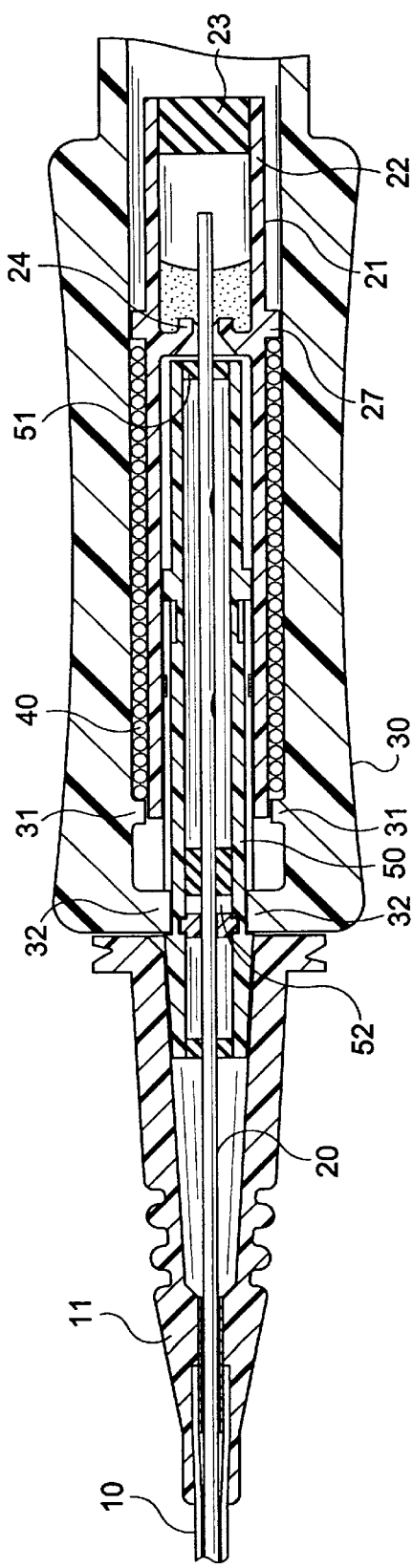

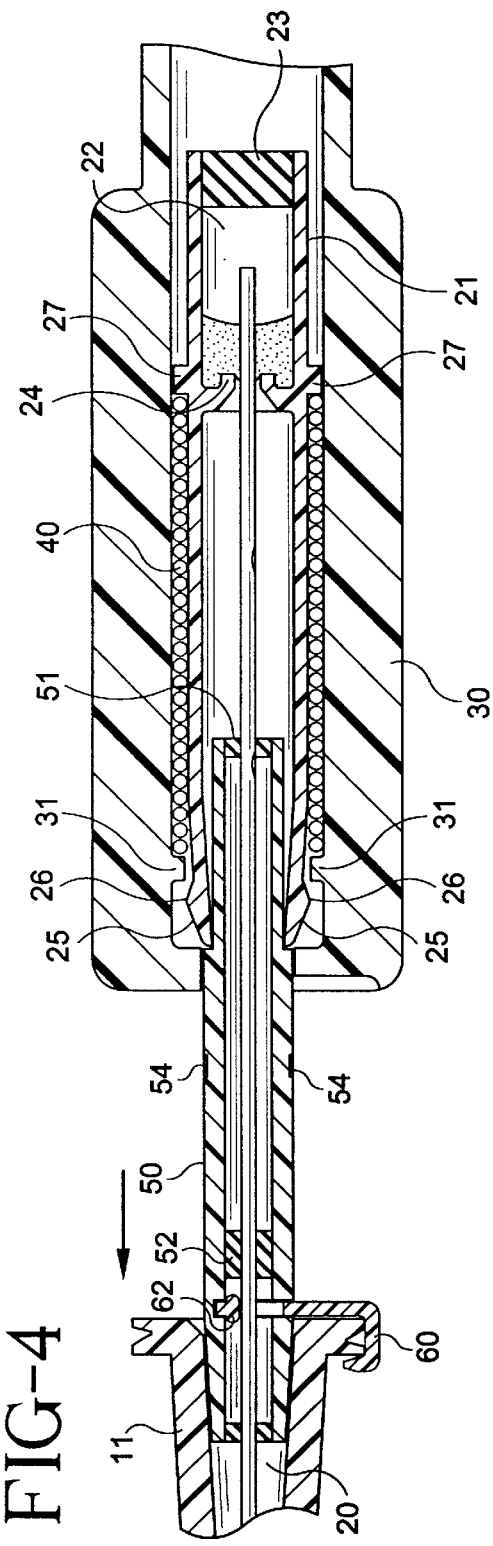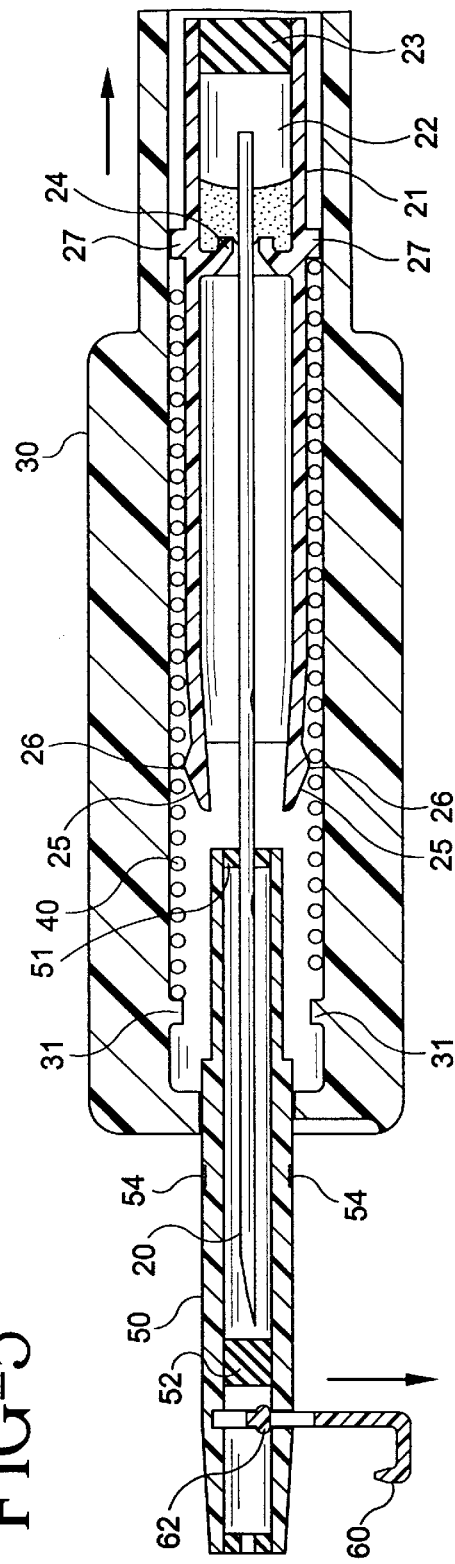

ONE STEP CATHETER ADVANCEMENT AUTOMATIC NEEDLE RETRACTION SYSTEM

This application is a continuation of U.S. Ser. No. 08/628,040 filed Apr. 4, 1996.

BACKGROUND OF THE INVENTION

This invention relates in general to an intravenous ("IV") catheter and introducer needle assembly having an automatic needle retraction system.

IV catheters are used to provide fluid to or withdraw fluid from a patient. In order to properly place an IV catheter in a patient's vein, a sharp introducer needle must be used to puncture the skin, tissue and vein wall to provide a path for placement of the catheter in the vein. Typical IV catheters are "over-the-needle" catheters where the catheter is coaxially placed over the needle. The catheter thus rides with the needle through the skin, tissue and vein wall and into the patient's vein. When the needle pierces the vein, blood will "flashback" into the needle and a flashback chamber typically located at the proximal end of the needle. Thus, once the medical technician observes this "flashback" of blood, the medical technician will know that the catheter and needle have been inserted in the vein. The needle can then be withdrawn from the patient and the catheter can be advanced further into the vein.

In recent years, there has been great concern over the immediate disposal of needles after use. This concern has arisen because of the advent of currently incurable and fatal diseases, such as Acquired Immune Deficiency Syndrome ("AIDS"), which can be transmitted by the exchange of body fluids from an infected person to another person. If a needle has been used to place a catheter in the vein of an AIDS infected person, the needle is a vehicle for the transmission of the disease. Thus, it is extremely important for a clinician to properly dispose of the needle to avoid a needlestick with the contaminated needle. Unfortunately, in certain medical environments, such as emergency situations, needlesticks with a contaminated needle can occur if the contaminated needle is not somehow covered immediately after use.

Much effort has been directed to develop an introducer needle assembly that can be shielded after use to minimize the possibility of an accidental needlestick with a contaminated needle. Some assemblies are deficient because the medical technician is required to perform an additional step in order to actuate the needle shielding system after the catheter has been properly located in the patient's vein. In addition, some assemblies are deficient because visualization of flashback is poor.

SUMMARY OF THE INVENTION

It is therefore an object of this invention to provide a catheter and needle introducer assembly where the needle can be shielded immediately after use.

It is another object of this invention to provide a catheter and needle introducer assembly that is easy to use.

It is yet another object of this invention to provide a catheter and needle introducer assembly where the needle can be shielded without the need for the medical technician to perform an extra step after the catheter has been properly located in the patient's vein.

It is still another object of this invention to provide a catheter and needle introducer assembly that has improved flashback visualization.

The one step catheter advancement automatic needle retraction system of the invention comprises a generally hollow barrel, a needle slidably disposed in the barrel so the sharp distal tip of the needle can initially extend beyond the distal end of the barrel and then can be retracted into the barrel, a needle hub having a generally hollow distal portion that extends adjacent to a portion of the needle, the needle hub may also include a flashback chamber fixed to the proximal end of the needle, a spring disposed between the needle hub and the barrel, a movable chamber disposed coaxially about the needle between the needle and the distal portion of the needle hub for initially maintaining the needle hub adjacent to the distal end of the barrel and a clip for maintaining the movable chamber adjacent to the catheter hub until the needle is retracted into the barrel. The barrel, needle hub and movable chamber are configured to cooperate in such a manner to initially hold the needle against the bias of the spring so the sharp distal tip of the needle extends beyond the distal end of barrel, yet allow the spring to force the needle hub and the needle toward the proximal end of the barrel when the barrel and catheter have been moved away from each other. This movement thus shields the sharp distal tip of the needle in the barrel and the movable chamber once the catheter and the barrel have been moved away from each other.

The above and other objects and advantages of the invention will be apparent upon consideration of the drawings and the following detailed description.

BRIEF DESCRIPTION OF THE DRAWINGS

The preferred embodiments are illustrated in the drawings in which like reference numerals refer to like elements and in which:

FIG. 1 is a perspective view of this invention with the catheter adjacent to the distal end of the barrel and the needle in the fully extended position prior to retraction into the barrel;

FIG. 2 is a side view in cross-section of this invention taken along line 2—2 in FIG. 1 with the needle in the fully extended position prior to insertion of the needle and catheter into a patient;

FIG. 3 is a cross-sectional view of this invention taken along line 3—3 in FIG. 1 with the needle in the fully extended position prior to insertion of the needle and catheter into a patient;

FIG. 4 is a side view in cross-section of this invention, similar to FIG. 2 but with the catheter advanced away from the distal end of the barrel prior to the needle being retracted into the barrel;

FIG. 5 is a side view in cross-section of this invention similar to FIG. 2 but with the catheter removed from the introducer needle assembly and the needle being retracted into the barrel;

DETAILED DESCRIPTION OF THE INVENTION

Figure 6:
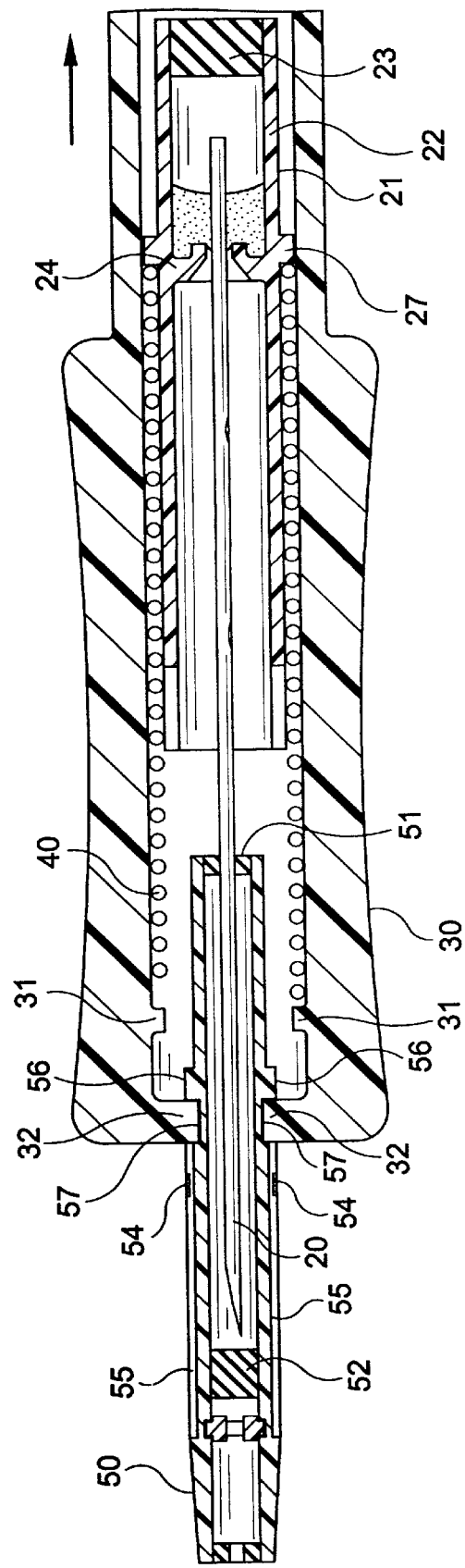
FIG. 6 is a cross-sectional view of this invention similar to FIG. 3 but with the catheter removed from the introducer needle assembly and the needle being retracted into the barrel.
Figure 7:
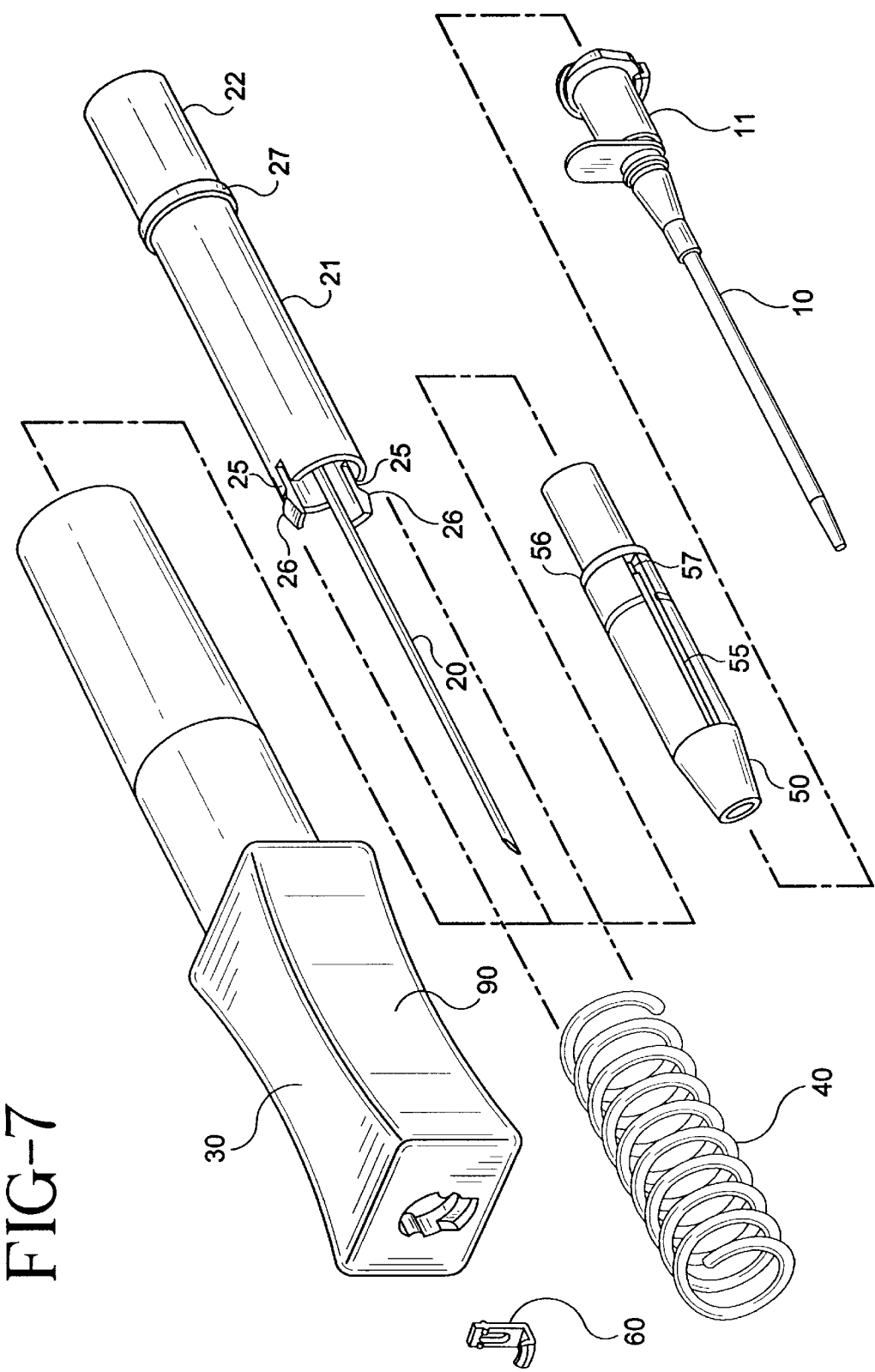
FIG. 7 is an exploded perspective view of this invention.
Figure 8:
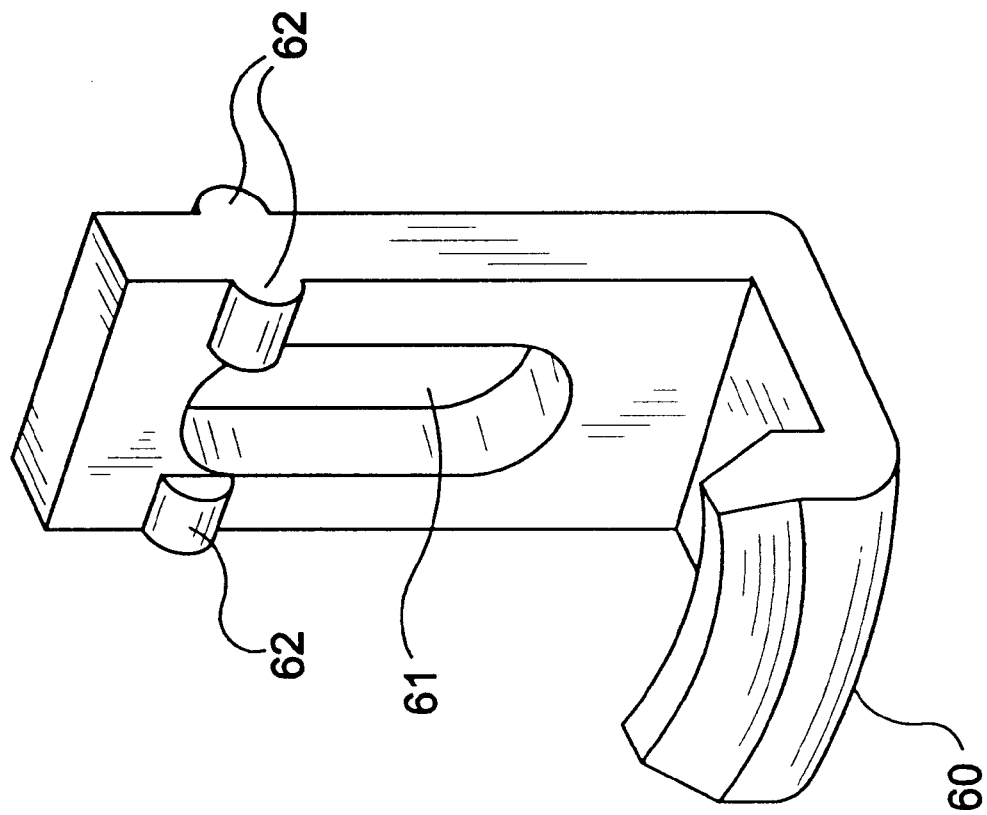
FIG. 8 is a perspective view of the clip used to connect the catheter to the introducer needle assembly until the needle has been retracted into the barrel.

The one step catheter advancement automatic needle retraction system of this invention can be seen generally in the FIGS. This system includes a catheter 10, a catheter hub 11, a hollow needle 20, a needle hub 21 which can include a flashback chamber 22, a barrel 30, a spring 40, a movable chamber 50 which can also act as a flashback chamber and a clip 60 that holds movable chamber 50 adjacent to catheter hub 11 until needle 20 has been retracted into barrel 30. Barrel 30 can include a contoured ergonomic handle 90 for ease of gripping.

Barrel 30 is generally hollow and has a proximal end and a distal end. The proximal end of barrel 30 is preferably closed to prevent the passage of needle 20, needle hub 21, spring 40 or chamber 50 from passing therethrough. However, the proximal end of barrel 30 should at least be perforated to allow air to escape from the interior of barrel 30 to facilitate retraction of needle 20 therein. The distal end of barrel 30 should be open to allow needle 20 and chamber 50 to slide therethrough. Barrel 30 also includes at least one inwardly extending shoulder 31 located adjacent to the distal end of barrel 30. This shoulder 31 serves two functions. First it acts as a stop against which the distal end of spring 40 can rest. Second it is part of the mechanism in conjunction with the configuration of needle hub 21 that is used to hold the needle hub against the force of spring 40.

Needle 20 is attached at its proximal end to needle hub 21. The proximal portion of needle hub 21 preferably defines a flashback chamber 22 to collect the blood that "flashes back" through needle 20 when the sharp distal tip of needle 20 pierces a patient's vein. The proximal end of flashback chamber 22 preferably is occluded by a vented closure, such as porous plug 23, to allow air but not blood to escape from flashback chamber 22 when blood enters. For example, a porous high molecular weight polyethylene such as the material sold under the POREX trademark by Porex Materials Corporation may be used. Alternatively, a thin perforated or slit impervious material can be placed over the proximal end of flashback chamber 22.

Needle hub 21 also includes an internal wall 24 having an aperture therein through which the proximal end of needle 20 extends. This wall 24 defines the distal end of flashback chamber 22. Needle 20 should fit snugly in this aperture so needle 20 is held in place by wall 24. Preferably an adhesive, such as a two-part epoxy or a UV curable glue, is placed around needle 20 and wall 24 adjacent to the aperture. This glue ensures that needle 20 remains fixed with respect to needle hub 21. It also provides a fluid tight seal at the distal end of flashback chamber 22 to prevent blood leakage therefrom.

The distal portion of needle hub 21 defines a generally hollow chamber surrounding a portion of needle 20. This hollow chamber includes at least one and preferably two flexible arms 25 having raised portions 26 thereon. Each raised portion 26 has an angled proximal outer surface. Preferably this angle is between about 30 degrees and about 45 degrees. The purpose of this configuration for raised portions 26 will be discussed below.

Needle hub 21 also defines an outwardly extending shoulder 27 adjacent to flashback chamber 22 to serve as a stop against which the proximal end of spring 40 can rest.

Spring 40 is disposed about the distal portion of needle hub 21 in the annular space between the distal portion of needle hub 21 and barrel 30 and between shoulders 31 and 27. When needle 20 is in the extended position with the sharp distal end of needle 20 extending beyond the distal end of barrel 30, spring 40 is in compression. In addition, when needle 20 is in this position, raised portions 26 are located on the distal side of shoulder 31. See FIG. 2. The angled raised proximal outer surface of raised portions 26 abut shoulder 31 to prevent spring 40 from moving needle hub 21 in a proximal direction toward the proximal end of barrel 30. When raised portions 26 are moved to the proximal side of shoulder 31, as discussed in more detail below, needle hub 21, and needle 20, will be urged away from the distal end of barrel 30 by spring 40 to retract the sharp distal end of needle 20 into barrel 30.

Chamber 50 is disposed about needle 20 inside the distal portion of needle hub 21. Chamber 50 has a larger outer diameter along its distal portion than along its proximal portion. The larger outer diameter of the distal portion of chamber 50 is sized to keep flexible arms 25 adjacent to the inner wall of barrel 30. This allows raised portions 26 to engage the distal end of shoulder 31 to prevent retraction of needle hub 21 and thus needle 20.

In addition, chamber 50 defines a proximal seal 51 and a distal seal 52. These seals define a fluid tight chamber therebetween which can serve as a secondary flashback chamber if a central portion of needle 20 were to define an opening for blood flow therethrough. This secondary flashback chamber allows the medical technician to view the flashback sooner because the secondary flashback chamber is located at a distal portion of the assembly. Seals 51 and 52 are self-sealing and should be sufficiently porous to allow air but not blood to escape. In addition, these seals allow chamber 50 to move along needle 20.

When chamber 50 is moved distally to a position where raised portions 26 are over the smaller outer diameter proximal portion of chamber 50, raised portions 26 can move radially inwardly so that they no longer engage shoulder 31. See FIG. 4. Raised portions 26 move radially inwardly due to the angled proximal outer surface. Because spring 40 is exerting a longitudinal force on raised portions 26 due to the location of spring 40 between shoulders 31 and 27, the angled proximal outer surface results in a component of the longitudinal force being a radially inwardly directed force applied to raised portions 26. Thus, when raised portions 26 are adjacent to the smaller outer diameter proximal portion of chamber 50, raised portions 26 are forced radially inwardly out of engagement with shoulder 31. At this point, spring 40 can retract needle hub 21 against the proximal end of barrel 30. Thus needle 20 is retracted inside chamber 50 and barrel 30 so that the sharp distal tip of needle 20 is located in chamber 50 and cannot accidentally stick a healthcare worker.

Chamber 50 can include markers 54 thereon to alert the user that chamber 50 is at the point where it will allow spring 40 to retract needle 20 into barrel 30. Markers 54 can be molded in, printed on or shrink wrapped on chamber 50. In addition, markers 54 could be in the form of one or more bumps formed on chamber 50 that can be felt by the healthcare worker or that interact with barrel 30 to produce an audible click. Chamber 50 may also include an upstanding push off tab located along a distal portion thereof so that the push off tab extends between the proximal end of catheter hub 11 and the distal end of barrel 30. This push off tab would facilitate the movement of catheter 10 away from barrel 30.

Chamber 50 also preferably defines a pair of longitudinally extending grooves 55 that engage a pair of short rails 32 formed in the distal end of barrel 30. This groove and rail arrangement prevents rotation of chamber 50 with respect to barrel 30 during longitudinal movement of chamber 50. This ensures that the medical technician is able to keep the bevel of the sharp distal tip of needle 20 in the proper orientation.

In addition, the proximal ends of grooves 55 include a stop portion that includes shoulders 56 and holes 57 that lock rails 32 of barrel 30 therein. This locks chamber 50 in the extended position when rails 32 drop into holes 57 to prevent unintended unsheathing of the sharp distal tip of needle 20 when needle 20 has been retracted. Alternatively, if barrel 30 were designed so it is long enough to completely shield the sharp distal tip of needle 20 therein, chamber 50 could be freely retracted into barrel 30 without the sharp distal tip of needle 20 being exposed after needle 20 is retracted.

J-shaped clip 60 may be located adjacent to the distal end chamber 50 distal of distal seal 52 to hold catheter hub 11 on the distal end of chamber 50 until needle 20 has been retracted into barrel 30. Clip 60 defines an opening 61 through which needle 20 extends. In this position, needle 20 prevents clip 60 from moving downwardly so that the hook portion of clip 60 securely engages the flange on catheter hub 11. When needle 20 has been retracted into barrel 30, clip 60 may move freely downwardly to disengage the hook portion from the flange on catheter hub 11 so catheter hub 11 can be removed from chamber 50. See FIG. 5. Internal grooves are formed in chamber 50 to provide a passageway for the movement of clip 60. Protrusions 62 are located on at least one and preferably both faces of clip 60, and preferably on both sides of opening 61. These protrusions 62 engage the surface of the passageway to prevent clip 60 from falling out of chamber 50 once needle 20 has been retracted into barrel 30.

The operation of the one step catheter advancement automatic needle retraction system will now be discussed.

After the venipuncture site on the patient has been prepared, the clinician grasps barrel 30 and inserts the sharp distal tip of needle 20 into the site. Barrel 30 is advanced until flashback in flashback chamber 22 is observed. At that point, the clinician advances catheter 10 off of needle 20 at the same time that barrel 30 is moved proximally to remove needle 20 from catheter 10. Because clip 60 is engaged with catheter hub 11, chamber 50 is extended from barrel 30 as catheter 10 is separated from barrel 30. See FIG. 4. Once the clinician sees, feels or hears markers 54 on chamber 50, the clinician ensures that catheter 10 is properly placed and needle 20 is no longer needed. If everything is in order, the clinician continues to separate barrel 30 from catheter 10 by retracting barrel 30 while holding catheter 10 in place. Raised portions 26 move radially inwardly out of engagement with shoulder 31 allowing spring 40 to move needle hub 21 to the proximal end of barrel 30. Once needle 20 has been retracted so its sharp distal tip is proximal of clip 60, clip 60 can move freely downwardly to disengage from catheter hub 11 so the introducer needle assembly can be separated from catheter 10. See FIG. 5. Once chamber 50 is in the fully extended position, rails 32 drop in holes 57 to lock chamber 50 in the fully extended position. See FIG. 6. Thus, the sharp distal end of needle is safely housed inside chamber 50. Alternatively, barrel 30 could be long enough so that when needle 20 is retracted, the sharp distal tip of needle 20 remains safely housed in barrel 30.

Thus, it can be seen that the one step catheter advancement automatic needle retraction system of this invention achieves the desired goal of providing a catheter and needle introducer assembly where the needle can be shielded immediately after use, which is easy to use, which does not require an additional step by the medical technician after the catheter has been properly located in the patient's vein and which improves flashback visualization.

What is claimed is:

1. A catheter and needle introducer assembly, comprising:

a barrel defining a barrel lumen and having a proximal end and a distal end with an opening therein;

a catheter having a proximal end and a distal end;

a catheter hub affixed to the proximal end of the catheter;

a needle disposed in the catheter and having a sharp distal tip and a proximal end;

a needle hub affixed to the proximal end of the needle and disposed in the barrel lumen;

at least one flexible arm affixed to the needle hub such that in a first position the flexible arm engages the barrel and the sharp distal tip of the needle extends distally of the distal end of the barrel through the opening coaxially within the catheter;

a spring having a proximal end and a distal end, the spring engaging the barrel and the needle hub to urge the needle hub toward the proximal end of the barrel; and a chamber separate from and movable with respect to the needle hub and the barrel disposed inside the distal portion of the needle hub and coaxially about the needle, the chamber having a proximal portion and a distal portion with the proximal portion having a smaller outer diameter than the distal portion so in the first position the distal portion is adjacent to the flexible arm to urge the flexible arm into engagement with the barrel and in a second position the proximal portion is adjacent to the flexible arm and allows the flexible arm to move out of engagement with the barrel.

2. The catheter and needle introducer assembly of claim 1 wherein the chamber includes a marker on the distal portion.

3. The catheter and needle introducer assembly of claim 1 further comprising a movable clip disposed in the chamber and adjacent to the distal end of the chamber for releasably securing the catheter hub to the chamber.

4. The catheter and needle introducer assembly of claim 3 wherein the clip defines an opening therethrough through which the needle extends and a hook portion engaging the catheter hub.

5. The catheter and needle introducer assembly of claim 4 wherein the chamber includes a marker on the distal portion.

6. The catheter and needle introducer assembly of claim 1 wherein the flexible arm includes a radially extending portion with an angled outer proximal surface.

7. The catheter and needle introducer assembly of claim 6 wherein the angled outer proximal surface is at an angle of between about 30 degrees and about 45 degrees.

8. The catheter and needle introducer assembly of claim 6 further comprising a movable clip disposed in the chamber and adjacent to the distal end of the chamber for releasably securing the catheter hub to the chamber.

9. The catheter and needle introducer assembly of claim 8 wherein the clip defines an opening therethrough, a hook portion and at least one protrusion thereon.

10. The catheter and needle introducer assembly of claim 9 wherein the chamber includes a marker on the distal portions adjacent to the proximal portions.

11. A catheter and needle introducer assembly, comprising:

a barrel defining a barrel lumen and having a proximal end and a distal end with an opening therein;

a catheter having a proximal end and a distal end;

a catheter hub affixed to the proximal end of the catheter;

a needle disposed in the catheter and having a sharp distal tip and a proximal end;

a needle hub defining a flashback chamber affixed to the proximal end of the needle;

a means engaging the barrel and the needle hub for biasing the needle hub toward the proximal end of the barrel;

a means for retaining the needle hub adjacent to the distal end of the barrel; and a means for allowing the means for biasing to force the needle hub toward the proximal end of the barrel.

12. A catheter and needle introducer assembly, comprising:

a catheter having a proximal end and a distal end;

a catheter hub affixed to the proximal end of the catheter;

a needle disposed in the catheter and having a sharp distal tip and a proximal end;

a needle hub affixed to the proximal end of the needle;

a needle shield disposed between the needle hub and the catheter hub; and a clip operatively connected to the needle shield and engaging the catheter hub.

* * * * *